(12) United States Patent  (10) Patent No.: US 7,656,346 B2
Nohmi  (45) Date of Patent: Feb. 2, 2010

(54) MILLIMETER WAVE IMAGE PROCESSOR AND MILLIMETER WAVE IMAGE PROCESSING METHOD

(75) Inventor: Hitoshi Nohmi, Tokyo (JP)

(73) Assignee: NEC Corporation, Tokyo (JP)

( * ) Notice: Subject to any disclaimer, the term of this patent is extended or adjusted under 35 U.S.C. 154(b) by 495 days.

(21) Appl. No.: 11/723,620

(22) Filed: Mar. 21, 2007

(65) Prior Publication Data

US 2007/0222671 A1 Sep. 27, 2007

(30) Foreign Application Priority Data

Mar. 24, 2006 (JP) ............................ 2006-083119

(51) Int. Cl.
*G01S 13/89* (2006.01)
(52) U.S. Cl. ........................... 342/179; 342/21; 342/22; 342/189; 342/194; 342/196
(58) Field of Classification Search ................... 342/21, 342/22, 27, 179, 189, 194–197
See application file for complete search history.

(56) References Cited

U.S. PATENT DOCUMENTS

| 5,880,777 | A | * | 3/1999 | Savoye et al. ............. 348/217.1 |
| 5,909,244 | A | * | 6/1999 | Waxman et al. ........... 348/222.1 |
| 6,762,709 | B2 | | 7/2004 | Kikuchi et al. |
| 7,385,552 | B2 | * | 6/2008 | Archer et al. ................ 342/179 |
| 7,402,794 | B2 | * | 7/2008 | Kim et al. .................... 250/250 |
| 2002/0044276 | A1 | * | 4/2002 | Stoner et al. ............. 356/141.1 |
| 2003/1173210 | | | 6/2003 | Kikuchi et al. |
| 2006/0049980 | A1 | * | 3/2006 | Archer et al. ................ 342/179 |
| 2007/0018089 | A1 | * | 1/2007 | Kim et al. .................... 250/250 |
| 2007/0222671 | A1 | * | 9/2007 | Nohmi ........................ 342/142 |

FOREIGN PATENT DOCUMENTS

| GB | 2 386 947 | A | | 10/2003 |
| GB | 2436454 | A | * | 9/2007 |
| JP | 06-331725 | | | 12/1994 |
| JP | 2003-177175 | A | | 6/2003 |
| JP | 2007256171 | A | * | 10/2007 |
| WO | WO 2007/054685 | A2 | | 5/2007 |

* cited by examiner

*Primary Examiner*—John B Sotomayor
(74) *Attorney, Agent, or Firm*—Foley & Lardner LLP

(57) ABSTRACT

A millimeter wave image processor, capable of performing imaging by matching and filtering while considering a spherical wave on an antenna face in a near field, is provided. The processor includes: a T-antenna which receives a radio wave emitted by a target; an A/D converter which A/D converts signals received by the T-antenna; a correlation processing unit which performs correlation processing to a combination of signals of a horizontal conversion output and a vertical conversion output among A/D converted data; and an imaging processor which correlates a reference function in which a received signal is generated theoretically on an assumption that the target is at a position of a focused distance and a received signal of a spherical wave received by the T-antenna for each pixel in the field of view to thereby create an image of the target.

7 Claims, 6 Drawing Sheets

MILLIMETER WAVE IMAGE PROCESSOR AND MILLIMETER WAVE IMAGE PROCESSING METHOD

BACKGROUND OF THE INVENTION

1. Field of the Invention

The present invention relates to a millimeter wave image processor and a millimeter wave image processing method, in which an electromagnetic wave of a millimeter wave emitted or reflected by a moving or still object is received, whereby image information of the object as a target is acquired.

2. Description of Related Art

A human body or the like may emit a millimeter wave together with an infrared ray. Further, every article emits and reflects an electromagnetic wave of a millimeter wave band at an intensity determined depending on the temperature and the radiative coefficient. The transparency of a millimeter wave with respect to moisture and substance is higher than the transparency of an infrared ray with respect to moisture and substance. By receiving such a millimeter wave so as to perform image processing, it is possible to monitor a target such as a distant landscape where is interrupted by fog and a near human body wearing a thick coat, and the like. This includes a case where an airplane makes a landing in the fog or a case of monitoring passengers passing through a security gate at an airport.

As a method of monitoring such a target, a method of monitoring by obtaining a visual image of high accuracy has been proposed as shown in Japanese Patent Application Laid-Open No. 6-331725 (Patent Document 1). The art shown in Patent Document 1 was developed considering the fact that image scanning within a field of view took time as accuracy became higher, whereby imaging of a moving object became difficult. To cope with it, in Patent Document 1, a plurality of receiving elements is provided to speed up scanning.

In Patent Document 1, in order to make an image highly accurate, the antenna aperture size must be large. However, in a large antenna of a millimeter wave band, extremely high machining accuracy is needed, and the manufacturing is difficult, and a thermal distortion error caused by temperature change in the used environment cannot be disregarded. Further, such an antenna is designed to obtain a narrow beam width and high gain in a far field, so if an object is in a near field, the resolution will be lowered after all. Moreover, in order to scan within a certain view angle with a large antenna of high resolution, the integral time per resolution cannot be obtained sufficiently as the beam width becomes acuter, so that the sensitivity is lowered. Therefore, it is difficult to obtain an image with high accuracy.

In view of the above, a radar system in which a phase error caused by antenna distortion and temperature characteristics of a cable is compensated has been developed, as disclosed in Japanese Patent Application Laid-Open No. 2003-177175 (Patent Document 2). In the art disclosed in Patent Document 2, a millimeter wave from an object is received by a two-dimensional plane antenna, and the received signal is converted by an A/D converter to digital data, and the digital signal is processed by a signal processor to thereby obtain image data. In Patent Document 2, prior to measurement, a calibration signal is output from the calibration signal source, and phase correction data is obtained by a compensator of the signal processing unit to thereby perform correction of measured data.

However, in the processing method disclosed in Patent Document 2, when monitoring a target positioned in a far field, an emitted signal from a target is viewed as a plane wave so as to be able to generate an image of sufficiently high resolution. However, when monitoring a target located in a near field, a signal from a target made incident on an antenna is close, so it is not considered as a plane wave. This causes a problem of unfocused image.

Further, as the frequency band width for the processing is wider, higher sensitivity can be realized. However, the phase delay difference among all antenna systems in the wide receiving band width must be small. This makes the manufacturing of the system difficult and expensive.

SUMMARY OF THE INVENTION

It is an object of the present invention to provide a millimeter wave image processor and a millimeter wave image processing method capable of, in the case of a far field where a target is significantly far compared with the antenna aperture size, generating a highly accurate image by conventional two-dimensional Fourier transformation processing, and in the case of a near filed where a target is near, generating a highly accurate image by performing imaging through correlation processing using a reference function.

Further, it is another object of the present invention to provide a millimeter wave image processor and a millimeter wave image processing method capable of performing phase correction for each antenna system independently and making phase characteristics the same upon all signal bands used for imaging in order to make manufacturing of devices easy.

An image processing method according to the present invention will be described based on FIG. 1. As antennas deployed in two dimensions, one in which a plurality of antennas 2 aligned vertically and horizontally are arranged to be in T shape on an antenna face 1 is taken as an example. Besides the T shape, various shapes such as L shape and triangle are acceptable. Hereinafter, the antennas 2 arranged to be in T shape on the antenna face 1 are correctively referred to as a T-antenna 2.

The present invention enables highly accurate imaging of a target by combining two phase correction methods, that is, in-band phase correction and antenna phase correction, and far field imaging processing or near field imaging processing depending on the distance to the target.

Note that the antenna face 1 is not always completely flat. Distortion may be caused due to changes in the environment temperature, mechanical stresses, or the like. When distortion is caused in the antenna face 1, the physical positioning relationship of the T-antenna 2 mounted on the antenna face 1 changes, whereby a difference is caused between phases of the radio wave received by the T-antenna 2. Thereby, highly accurate image data cannot be acquired.

In view of the above, the phase correction method of the present invention takes into account that the value calculated by dividing the distance R from the target 4 to the T-antenna 2 by the wavelength $\lambda$ is a phase $\emptyset$ of a radio wave received by each antenna of the T-antenna 2, and the phase of a radio wave received by each antenna of the T-antenna 2 is calculated based on an equation in which the distance R from the calibration signal generator 5 to each antenna of the T-antenna 2 is divided by the wavelength $\lambda$, that is, $\emptyset = R/\lambda$. Then, a difference between the observed phase of the radio wave and the calculated phase of the radio wave is acquired, whereby distortion in the antenna face 1, that is, the phase of the radio wave received by each antenna of the T-antenna 2, is corrected.

Information of the observed phase of the radio wave is acquired as follows. That is, since the distance from the calibration signal generator 5 to each antenna of the T-antenna and the position thereof have been known, a subtle radio wave of a millimeter wave band is emitted from the calibration signal generator 5 to the T-antenna 2, and the radio wave is received by each antenna of the T-antenna 2 and A/D-converted, and then correlation integral processing is performed between the signals of all antennas of the T-antenna 2, whereby observed data of the phase difference between the respective antennas is acquired.

From the difference between the observed phase information and the phase information calculated by a theoretical calculation, positioning distortion of each antenna and phase distortion amount due to electric length difference (phase delay) of receiving systems are estimated, and an antenna phase distortion correction function is created to thereby compensate signals of the time delay of observation.

Another phase distortion causing deterioration in an image is signal frequency band phase distortion. This is caused due to a fact that in each receiving system of an antenna of the T-antenna 2, phase characteristics determined by the frequency within the receiving band from the T-antenna to the A/D conversion are different in the vertical and horizontal antennas 2a and 2b of the T-antenna 2. The phase characteristics can be measured by using the calibration signal generator 5. By changing the transmitting frequency from the upper limit to the lower limit frequency in the signal band by the same test calibration as that described above, and by performing correlation integral processing to a combination of received signals of the reference vertical and horizontal antennas 2a and 2b, a phase frequency characteristic D1 of the vertical and horizontal antennas 2a and 2b is measured. Then, as shown in FIG. 4, a filter function D2 of an inverse frequency characteristic of the characteristic D1 is Fourier-transformed. Thereby, a filter coefficient D3 of a time function is generated, and computation is performed to the A/D-converted data as a transversal filter, whereby signal in-band phase correction is performed.

Then, depending on the distance between the target 4 and the T-antenna 2, a radio wave from the target 4 received by the T-antenna 2 is considered, and imaging processing by the imaging processor 13 is switched As shown in FIG. 1, assuming that the total aperture size of the antenna 1 on the T-antenna 2 is D, and the distance from the T-antenna 2 to the target 4 is R, if $R<2D^2/\lambda$, that is, in the case of a near field (distance R1), the radio wave form received by the T-antenna 2 is a spherical wave. If $R>2D^2/\lambda$ (distance R2), that is, in the case of a far field, the radio wave form received by the T-antenna 2 can be considered as a plane wave.

Assuming that the opening dimension of the antenna face 1 is 50 cm and the frequency of a radio wave from the target 4 is 94 GHz, the wavelength $\lambda$ is about 3 mm, so the distance $R=\{2*(0.5)^2\}/0.0003=166.7$ m. Therefore, it can not be considered that the wave front from the target 4 is as a plane wave for the 50 cm aperture size antenna unless the distance between the target 4 and the T-antenna 2 is not less than about 166 m. If the target 4 is in the near field, for example, at a position of 5 to 6 m, blur will be caused in imaging by the conventional two-dimensional FFT.

In view of the above, in the imaging processing of the millimeter wave image processor according to the present invention, the type of a radio wave received by the T-antenna 2, that is, a spherical wave or a plane wave, is specified corresponding to the distance R between the T-antenna 2 and the target 4 based on the aperture size of the antenna face 1, and corresponding to the distance from the target 4 to the T-antenna 2, processing is selected by switching depending on whether the type of a radio wave received by the T-antenna 2 is a spherical wave or a plane wave.

Namely, a millimeter wave image processor according to the present invention includes: a T-antenna which receives a radio wave emitted by a target; an A/D converter and receiver which A/D-converts a signal received by the T-antenna; a correlation processing unit which performs correlation processing to a combination of signals of horizontal output and vertical output of A/D-converted data; and an imaging processor which creates an image of the target by correlating an correlation processing output of a spherical wave received by the T-antenna with a reference function, the reference function being a received signal theoretically generated on an assumption that the target is at a position of a focused distance, for each pixel in a field of view.

Further, the millimeter wave image processor includes an in-band phase characteristic corrector which performs phase correction to an output of the A/D converter with a transversal filter by a phase correction function previously measured, and makes phase characteristics of the respective antennas the same. Further, the millimeter wave image processor also includes an antenna phase characteristic corrector which compensates phase distortion of a received signal by using an antenna phase distortion correction function generated based on a phase difference of radio wave between a reception processing phase observed value provided from a calibration signal generator and a theoretical value.

According to the present invention, a radio wave from a target is received, and the received signal is A/D-converted. Then, after performing in-band phase correction computation to the A/D-converted data such that the phase characteristics of the vertical and horizontal antennas 2a and 2b of the T-antenna 2 become equal, correlation processing is performed to a combination of signals of a horizontal output and a vertical output. Further, by complex-multiplying the antenna phase distortion correction function, generated based on a difference between the observed correlation output phase when the calibration signal from calibration signal generator 5 receives and a phase of a theoretical value calculated from the position of the calibration signal generator, by the correlation output, changes of the distortion and electric length (phase delay) of the T-antenna 2 and a connection cable are compensated.

A signal after the phase distortion correction has been performed is processed by the imaging processor, whereby the target shape is imaged. In imaging, different methods are used for imaging a far object and for imaging a near object.

If a target is in a far field, two-dimensional FFT is performed to two-dimensional output data which is correlation-processed for all combinations of the signals received by the vertical and horizontal antennas 2a and 2b of the T-antenna 2, whereby imaging is performed. In contrast, if a target is in a near field, a reference function is theoretically generated on an assumption that the target is present in each pixel in the field of view having a distance to be focused. Reference functions are prepared by the number of pixels to be output in the imaging processing. Then, the correlation processing output of a spherical wave received by the T-antenna 2 and the reference function are correlated to thereby calculate an output of each pixel. Thereby, imaging of the target 4 is performed.

The T-antenna may adopt a configuration in which a plurality of antennas are aligned horizontally and vertically to be in T shape to thereby receive a radio wave, or a configuration in which at least two sets of antennas are linearly moved horizontally and vertically to form a T-shaped trajectory to thereby receive a radio wave.

EFFECT OF THE INVENTION

As described above, according to the present invention, in a passive method in which a target is monitored by receiving a millimeter wave of 94 GHz for example, it is possible to acquire clear image data irrespective of the target distance, from very near to far distance, to the two dimension antennas deployed vertically and horizontally. Further, even if the antennas or receiving systems are subject to environmental temperature changes and mechanical distortion and the received signals are subject to phase distortion, it is possible to compensate phase distortion to thereby acquire highly accurate image data constantly.

Further, even if the phase characteristic within the signal frequency band used for imaging are differ from one antenna element to another, highly accurate image can be generated constantly by phase correction. This enables to ease the required specification of hardware, to expand the frequency band usable for imaging, and to realize high sensitivity.

DESCRIPTION OF PREFERRED EMBODIMENTS

Hereinafter, an embodiment of the present invention will be described in detail based on the drawings.

Figure 2:
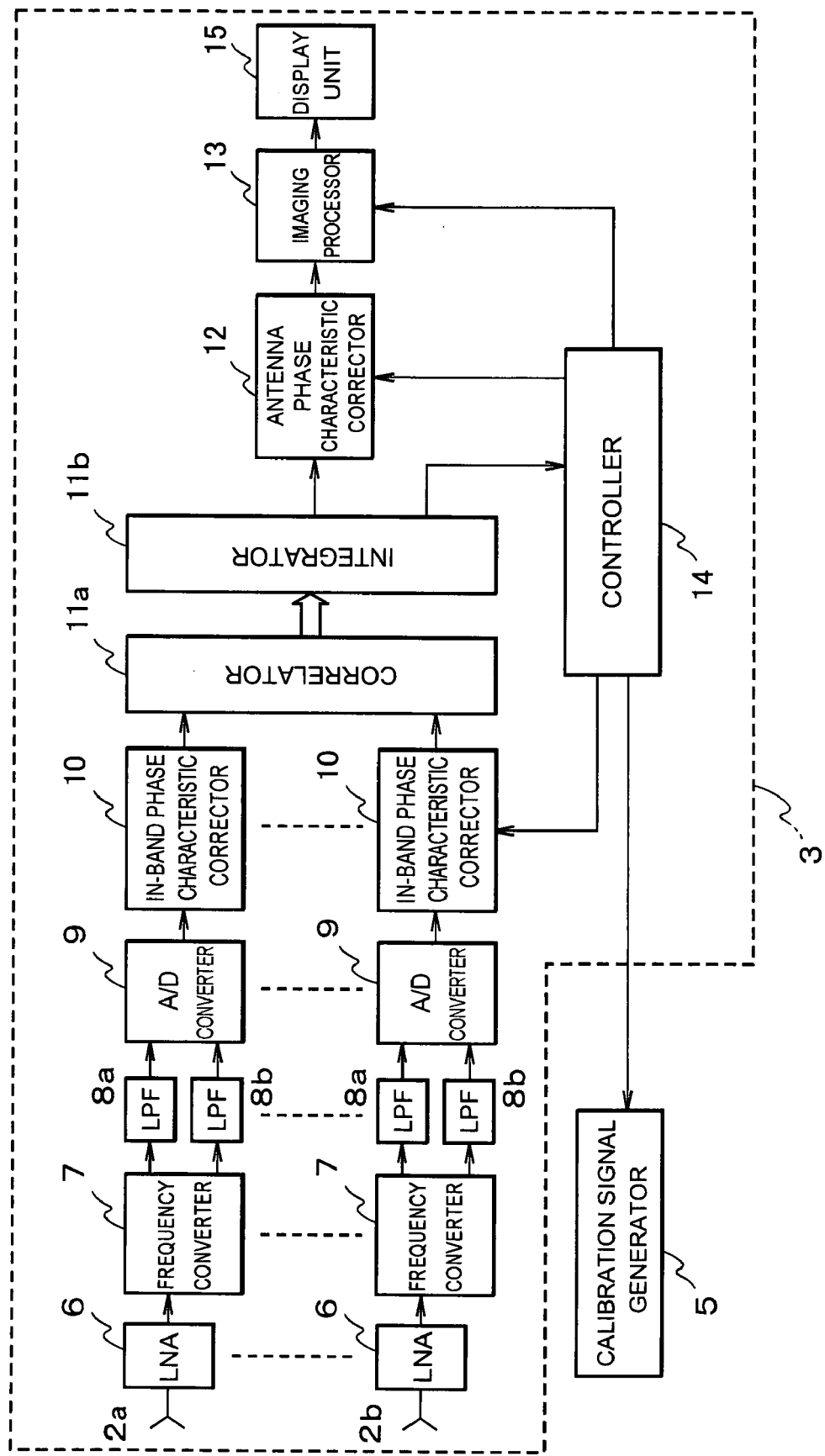
FIG. 2 is a diagram showing the configuration of the millimeter wave image processor according to the embodiment of the present invention.

As shown in FIG. 2, a millimeter wave image processor according to an embodiment of the present invention includes a reception processing display unit 3 and a calibration signal generator 5.

The calibration signal generator 5 is disposed at a position having a known distance from antennas 2, deployed two-dimensionally, of the reception processing display unit 3. The calibration signal generator 5 is so configured as to transmit a millimeter wave, to the antennas 2.

Figure 1:
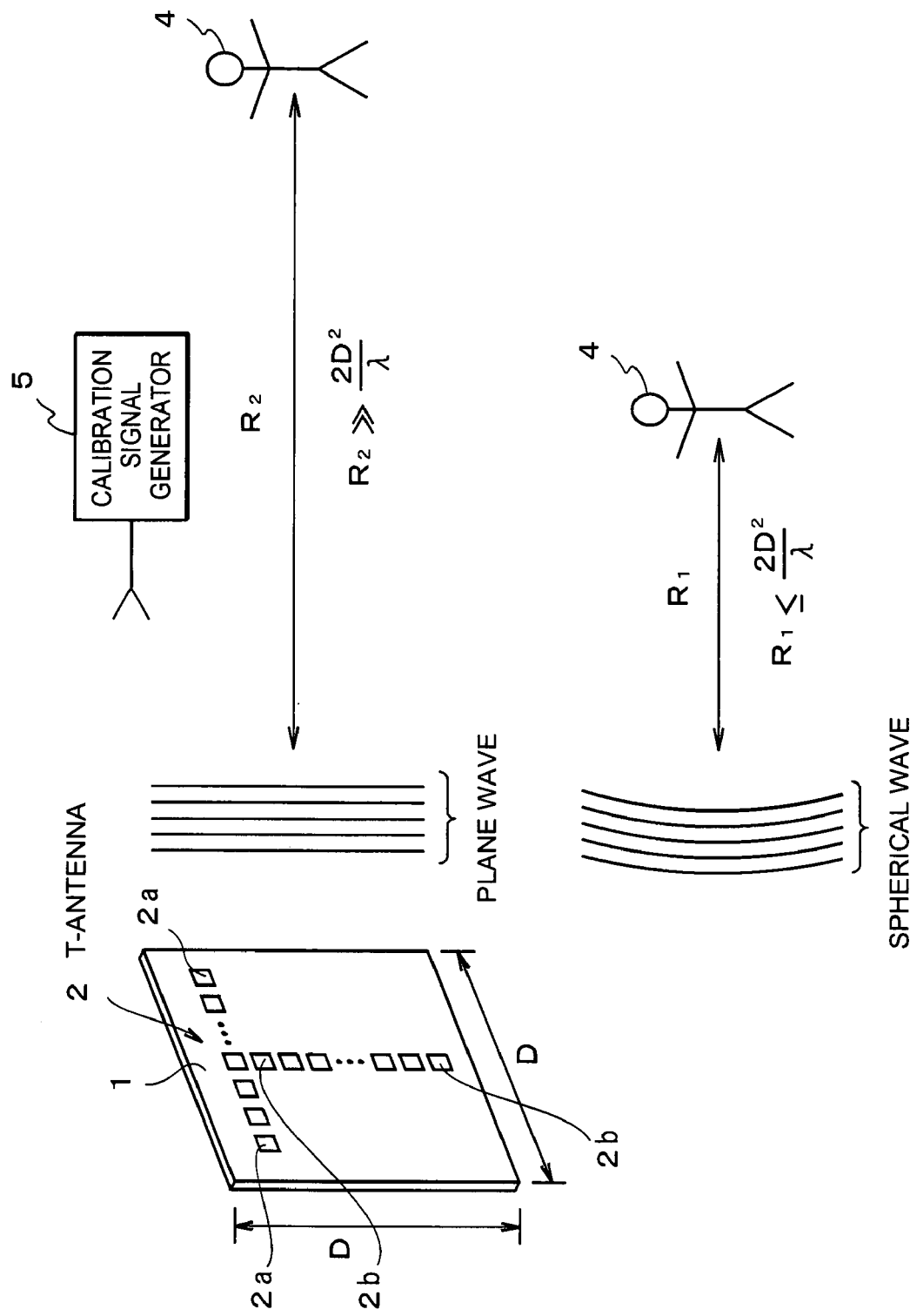
FIG. 1 is a diagram showing an operational configuration of a millimeter wave image processor according to an embodiment of the present invention.

As shown in FIG. 1, the reception processing display unit 3 has an antenna in which a plurality of antennas 2 are arranged in T shape on an antenna face 1, as an example of most simple calibration of antennas deployed two-dimensionally. Hereinafter, the antennas 2 arranged in T shape on the antenna face 1 are collectively referred to as a T-antenna 2. The T-antenna 2 consists of a plurality of horizontal (H-system) antennas 2a aligned horizontally on the antenna face 1, and a plurality of vertical (V-system) antennas 2b aligned vertically on the antenna face 1. The H-system antennas 2a and the V-system antennas 2b are combined to be in T shape as shown in FIG. 1. Note that the T-antenna 2 shown in FIG. 1 is so configured that a plurality of antennas 2a and 2b are aligned horizontally and vertically to be in T shape to thereby receive a radio wave, but it is not limited to this configuration. A configuration in which at least two sets of antennas 2a and 2b are linearly moved horizontally and vertically so as to form a T-shape trajectory to thereby receive a radio wave may be adopted.

In the T-antenna 2 built in the reception processing display unit 3, each antenna includes a receiver having an almost same electrical specification. As shown in FIG. 2, the receiver includes a low noise amplifier (LNA) 6, a frequency converter 7, a pair of lowpass filters 8a and 8b, an A/D converter 9, and an in-band phase characteristic corrector 10. Such a configuration is provided independently for each system of the horizontal antennas 2a and the vertical antennas 2b.

Further, the reception processing display unit 3 includes a correlator 11a and an integrator 11b to which data of all systems of the T-antenna 2 are input, and also includes an antenna phase characteristic corrector 12 which compensates the phase of output signal of the integrator 11b, an image processor 13, a display unit 15 and a controller 14 which generates phase characteristic functions.

The low noise amplifier 6 amplifies a received signal to be output from the T-antenna 2. The frequency converter 7 performs frequency conversion to a received signal, received by the T-antenna 2, with a local signal which is phase-synchronized such that the systems of the horizontal and vertical antennas 2a and 2b become coherent, and outputs an IQ signal (analog signal) which is a baseband complex signal from the received signal of each antenna 2a or 2b, and an I signal thereof is output to the lowpass filter 8a and the remaining Q signal is output to the other lowpass filter 8b, respectively.

The lowpass filters 8a and 8b perform band restriction such that the IQ output signal of the frequency converter satisfies sampling theorem with respect to the sampling frequency of A/D conversion to thereby remove high frequency components. The A/D converter 9 A/D-converts the analog IQ signal (received signal), in which the high frequency components are removed by the lowpass filters 8a and 8b, to a digital signal.

The in-band phase characteristic corrector 10 outputs the digital signal from the A/D converter 9 to the correlation processing unit 11 in a through state, and when a filter coefficient D3 of a time function is set in the controller 14 described later, the in-band phase characteristic corrector 10 performs transversal filter computation for the digital signal from the A/D converter 9, which was received by the T-antenna 2 and demodulated, based on the filter coefficient D3 such that the phase characteristics in the baseband frequency band used for imaging become equal in the systems of all horizontal and vertical antennas 2a and 2b, and outputs the output signal thereof to the correlator 11a and the integrator 11b.

The correlator 11a and the integrator 11b perform correlation integral processing to output signals from the in-band phase characteristic correctors 10 to a combination of signals of H-system antennas 2a and the V-system antennas 2b, that is, an output of vertical system and an output of horizontal system.

The controller 14 obtains the output from the integrator 11b as uncompensated phase characteristic data D1 between the systems of the vertical and horizontal antennas 2a and 2b, and generates a filter function D2 having inverse frequency characteristics of the uncompensated phase characteristic data D1 as a filter coefficient D3 of a time function by Fourier transformation. The controller 14 sets the filter coefficient D3 in the in-band phase characteristic correctors 10 of the vertical and horizontal antennas 2a and 2b. Further, the controller 14 generates an antenna phase characteristic correction function D4 based on the phase characteristic data D1, and sets the antenna phase characteristic correction function D4 in the antenna phase characteristic corrector 12.

The antenna phase characteristic corrector 12 complex-multiplies the correlated output from the correlator 11a and the integrator 11b by the antenna phase characteristic correction function D4 to thereby compensate changes in distortion of the T-antenna 2 and the electric length (phase delay), and distortion due to a cable connecting the antenna 2 and the reception signal processor 3 and the electric length (phase delay).

The imaging processor 13 has a two-dimensional FFT processing function for image-processing used in the case of far field where a target is distant, a reference function generating function for image-processing used in the case of near field, and a correlation processing function to correlate the correlated output from the correlator 11a and the integrator 11b, received by the T-antenna 2 and processed, and the reference function to thereby create an image of the target, based on an instruction from the controller 14. The imaging processor 13 generates a correlation integral output theoretically generated on an assumption that a point target is at a position of a focused distance as the reference function, for each pixel in the field of view. The display unit 15 displays the display signal from the imaging processor 13 as a visible image.

Next, description will be given for a case of performing image processing for a millimeter wave from a target using the millimeter wave image processor according to the embodiment of the present invention shown in FIG. 2.

First, in the present embodiment, a millimeter wave received by the T-antenna 2 is a plane wave. That is, as shown in FIG. 1, description will be given for a case where the target 4 is at a position having a distance R2 which is far from the T-antenna 2.

Each of the signals received by the H system and the V system of the T-antenna 2 is amplified by the low noise amplifier 6, and the amplified received signal is input to the frequency converter 7. The frequency converter 7, corresponding to all vertical and horizontal antennas 2a and 2b, frequency-converts the received signal of the T-antenna 2 to a signal of baseband frequency (baseband signal). The electric length (phase delay) of every low noise amplifier 6 is stable, and every frequency converter 7 performs the frequency conversion by using a local signal in which the phase is completely synchronized across the all vertical and horizontal antennas 2a and 2b.

When the A/D converter 9 receives the baseband signal from a plurality of frequency converters 7, it converts the baseband signal, which is an analog signal, to a digital signal, and outputs the baseband signal which is a digital signal to the in-band phase characteristic corrector 10.

The in-band phase characteristic corrector 10 outputs the digital signal from the A/D converter 9 to the correlation processing unit 11 in a through state, and based on the correction function from the controller 14, performs transversal filtering to the baseband signal as a digital signal to thereby compensate it such that the phase characteristic in the baseband becomes constant between the respective antenna systems.

The correction function is generated in the following manner. That is, first, the calibration signal generator 5 changes the origination frequency from the upper limit frequency to the lower limit frequency in the signal band, and emits it to the T-antenna 2. To the digital signal from the A/D converter 9 output by the in-band phase characteristic corrector 10 in a through state, the correlation processing unit 11 performs correlation processing, and the controller 14 acquires an output from the integrator 11b as uncorrected phase characteristic data between the systems of the vertical and horizontal antennas 2a and 2b.

Figure 4:
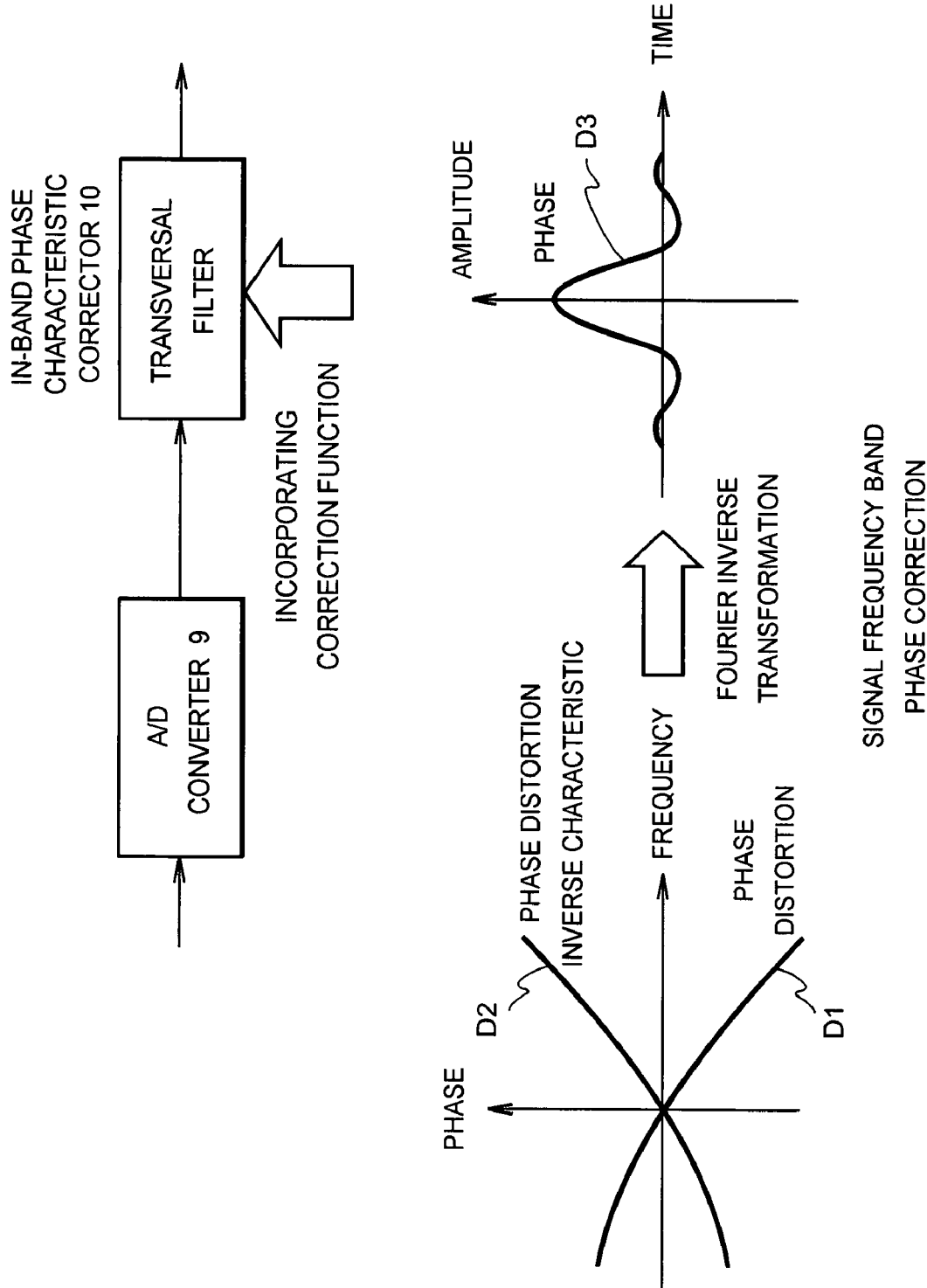
FIG. 4 is a diagram showing an operation of signal frequency in-band phase correction of the millimeter wave image processor according to the embodiment of the present invention.

As shown in FIG. 4, the controller 14 generates the filter function D2 which is an inverse frequency characteristic of the uncorrected phase distortion characteristic data D1 as the filter coefficient D3 of time function by Fourier transformation. The controller 14 sets the filter coefficient D3 in all in-band phase characteristic correctors 10 corresponding to the vertical and horizontal antennas 2a and 2b. As shown in FIG. 4, the in-band phase characteristic corrector 10 performs computation by using the filter coefficient D3 as a transversal filter to the A/D converted data to thereby perform in-band phase correction.

Processing in the correlator 11a, the integrator 11b and the antenna phase characteristic corrector will be described based on FIG. 3.

First, description will be given for a case where the correlator 11a performs correlation processing between received signals of the H-system antennas 2a and V-system antennas 2b of the T-antenna 2.

Figure 3:
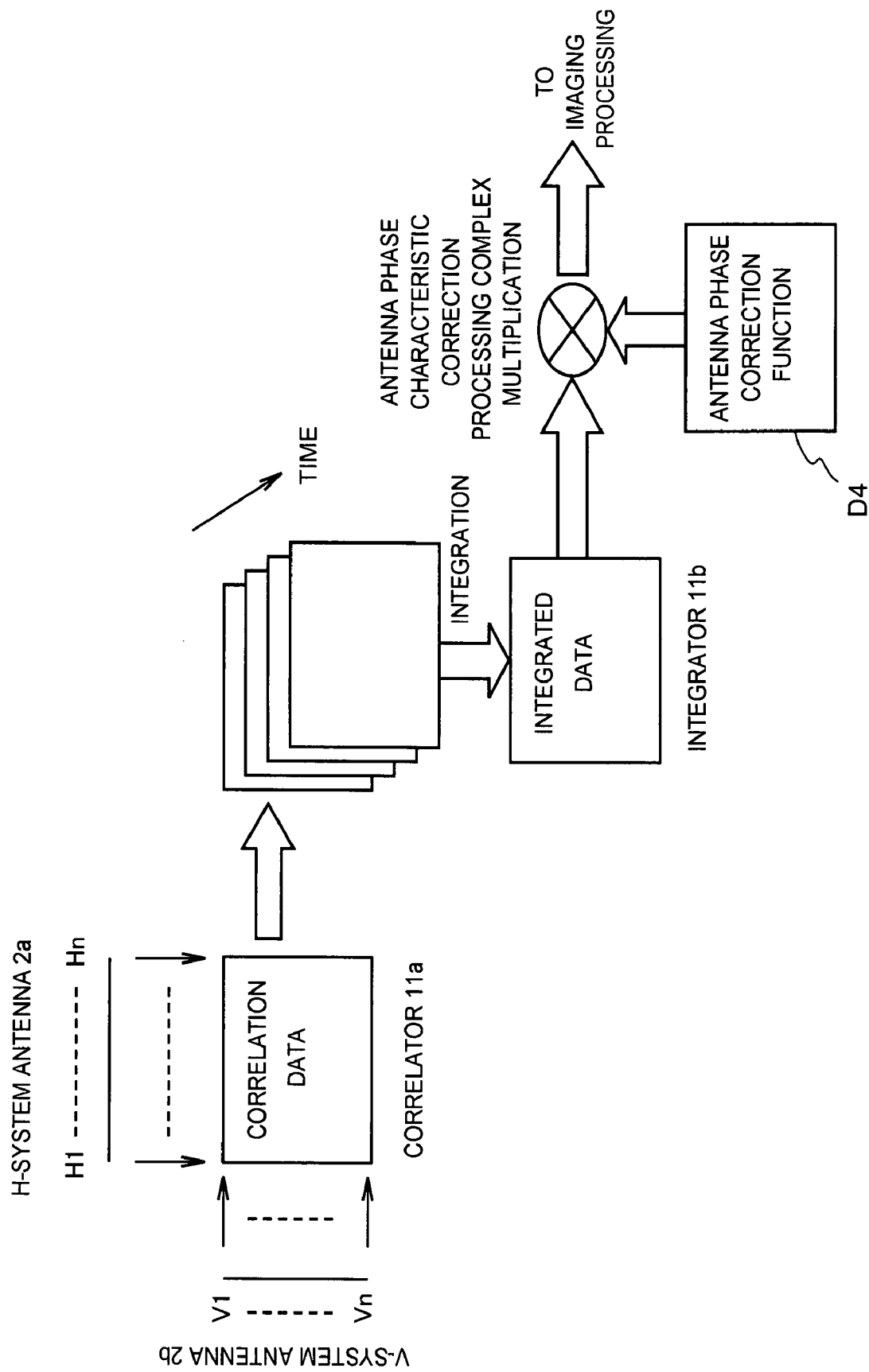
FIG. 3 is a configuration diagram showing correlation integral processing and antenna phase characteristic correction processing of the millimeter wave image processor according to the embodiment of the present invention.

As shown in FIG. 3, the correlator 11a performs correlation processing between the signals of the H-system antennas 2a and the V-system antennas 2b. The correlation processing by the correlator 11a determines a phase plane made incident on the antenna face 1 which is vector-synthesized by all signals from targets in a far field. The phase plane is calculated with the correlation among all antenna systems of the H-system antennas 2a and the V-system antennas 2b.

The correlator 11a performs correlation processing for all combinations of the H-system antennas 2a and the V-system antennas 2b to thereby obtain two-dimensional correlation data D4 as shown in FIG. 3. The integrator 11b performs integration for a long time to the signals which have been correlation-processed by the correlator 11a, and acquires integral data D5 as shown in FIG. 3. As a result of integration by the integrator 11b, internal noises caused inside the receiver corresponding to the T-antenna 2 are suppressed, whereby even a weakest received signal not more than the internal noise level can be imaged. If there is common spurious noise inside the receiver, the spurious would be extracted in the correlation integral processing. Therefore, as a local signal of the receiver in the reception signal processor 3, it is desirable to use a phased lock generator unit not to contain synchronized spurious.

The integral data output from the integrator 11b is complex-multiplied by the two-dimensional correction function by the antenna phase characteristic corrector 12 to thereby compensate mechanical distortion of antennas and phase distortion components due to distortion of cable length, and is output to the imaging processor 13.

The imaging processor 13 processes data from the antenna phase characteristic corrector 12 to thereby cause the display unit 15 to display image data of the target 4.

Figure 5:
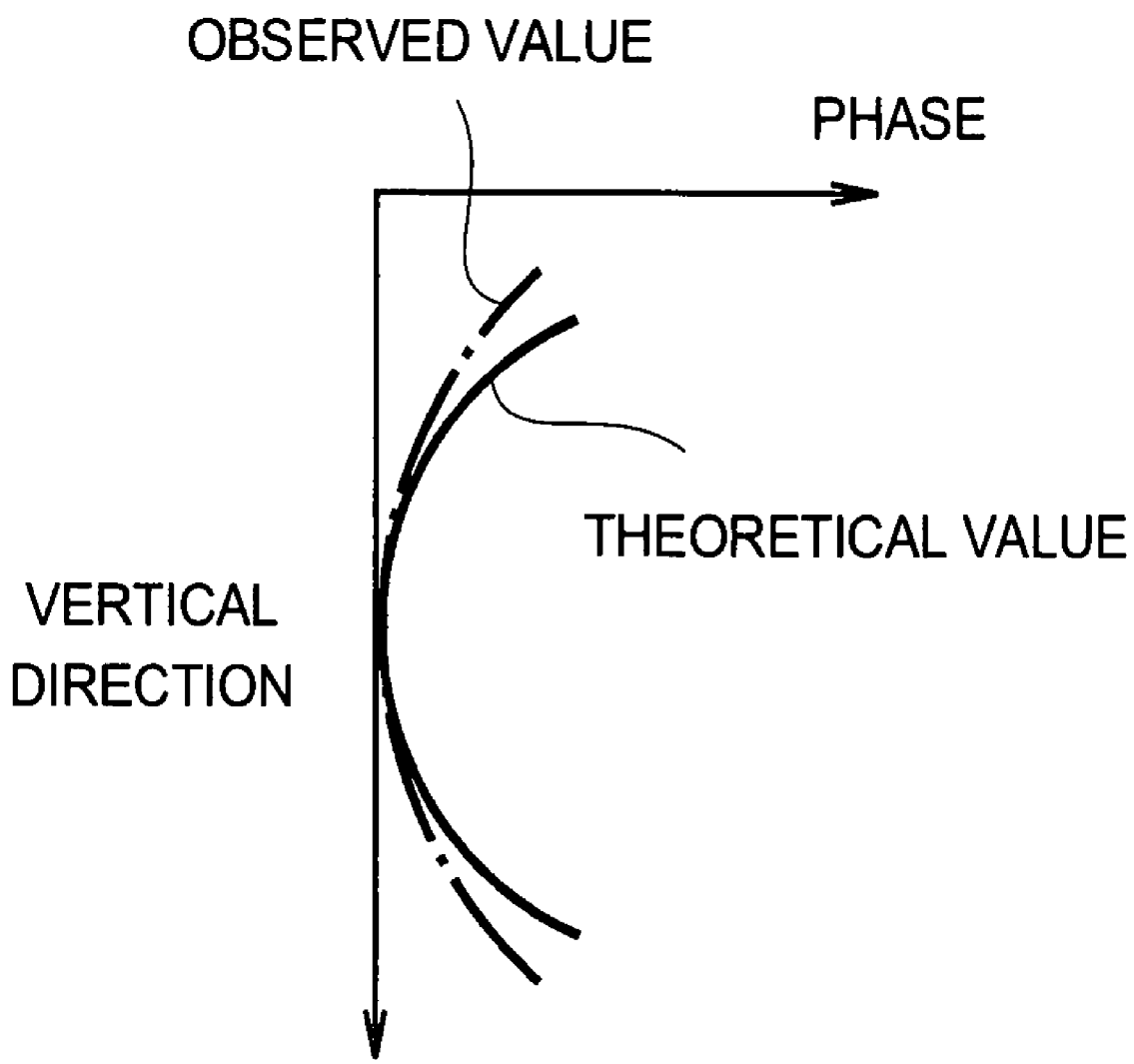
FIG. 5 is a diagram illustrating a phase shift between an observed value and a theoretical figure.

In the antenna face 1, distortion is caused due to a temperature change or mechanical stresses. If the distortion is caused in the antenna face 1, the physical positional relationship of the T-antenna 2 mounted on the antenna face 1 will be changed. As a result, a difference is caused between the calculated phase plane T1 of a millimeter wave received by the T-antenna 2 and the observed phase plane T2 of the millimeter wave as shown in FIG. 5. Thereby, a highly accurate image data cannot be obtained. For example, in the case of using a millimeter wave band of 94 GHz, when the antenna face 1 is distorted by 87 micron, phase error of 10 degrees is caused, which is appeared as deterioration of image. In order to compensate the phase error, an output of the calibration signal generator 5 is received by the T-antenna 2, and the difference between the received phase and the theoretical value is calculated by the controller 14, whereby correction is performed by the antenna phase characteristic corrector 12.

The theoretical value of the phase correction is calculated as follows. That is, since a value that a distance R from the target 4 to the T-antenna 2 is divided by a wave length λ is a phase ø of a radio wave received by the T-antenna 2, the theoretical value is calculated in accordance with an equation in which the distance R from the target 4 to the T-antenna 2 is divided by the wave length λ, that is, ø=R/λ.

Next, as shown in FIG. 1, description will be given for imaging processing when the target 4 is at a position having a distance R1 in a near field with respect to the T-antenna 2 in the present embodiment.

For the emitted signal from the target 4 received by the vertical and horizontal antennas 2a and 2b, the received signals of the vertical and horizontal antennas 2a and 2b are correlation-computed in the correlator 11a and the integrator 11b. In FIG. 3, if the target is in the far field, the two-dimensional correlation data output by the integrator 11b shows actual phase plane distribution on the antenna face, but if the target is in the near field, it shows a composite phase plane which is completely different from the actual phase plane pattern. Therefore, in order to obtain an image of the target 4 from the correlation data, correlation processing using a reference function must be performed.

Figure 6:
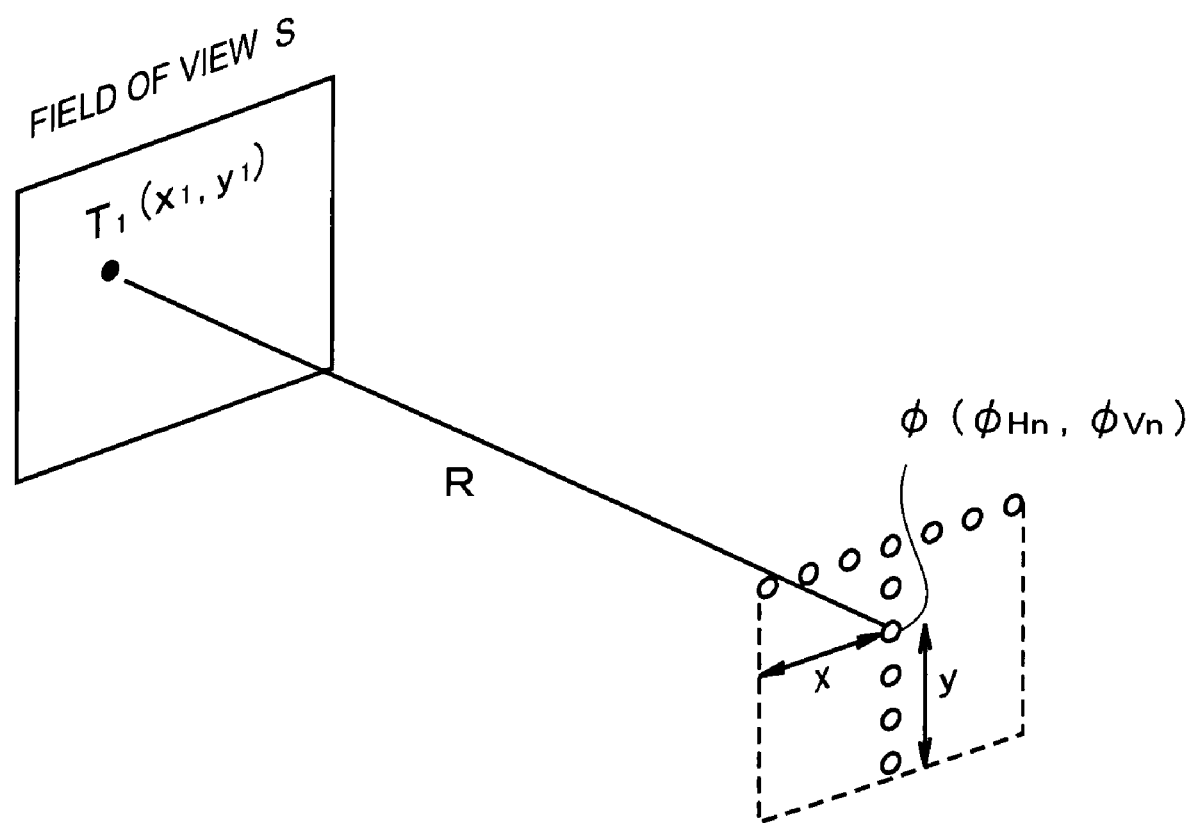
FIG. 6 is a diagram illustrating processing using a reference function.

Processing using the reference function is performed by the imaging processor 13. As shown in FIG. 6, the imaging processor 13 estimates the distance (focused distance) R1 to the target 4, and based on the distance R1, calculates the phase ø (øHn, øVn) on the antenna face 1 when a point target T1 (x1, y1) radiating the millimeter wave exists at a specific point on the view plane S. The phase ø is calculated from R1/λ.

The imaging processor 13 calculates the phase signal as a reference function on an assumption that correlation processing has been performed for the received signal by the vertical and horizontal antennas 2a and 2b. Then, the imaging processor 13 performs matched filter processing (performing multiplication between received signal and complex conjugate of reference function and integration) and outputs a data as an output component of the position of a point target initially assumed when the reference function generates.

The processing described above is performed on the whole surface of the view plane S to be imaged. For each pixel inside the view, by using a reference function theoretically generated on the assumption that the target is at a specific position of focused distance, the imaging processor 13 performs matched filter processing for the received signal of a spherical wave by the T-antenna to thereby create an image of the target, and outputs the image signal to the display unit 15.

Therefore, according to the embodiment of the present invention, in a passive system in which a target is monitored by receiving a millimeter wave of 94 GHz band for example, clear image data can be obtained irrespective of the distance of the target to the T-antenna. Further, even if the antenna or receiving systems are subject to environmental temperature change or mechanical stresses, and received signals are subject to phase distortion, it is possible to compensate phase distortion to thereby constantly obtain image data with high accuracy.

Further, even if the phase characteristics within the signal frequency band used for imaging differ from one antenna element to another, it is possible to constantly generate an image with high accuracy by phase correction. This enables to ease the required specification of hardware, to expand a frequency band to be used for imaging, and to realize high sensitivity.

INDUSTRIAL APPLICABILITY

As described above, according to the present invention, in a passive system in which a target is monitored by receiving a millimeter wave of 94 GHz band for example, clear image data can be obtained irrespective of the distance of the target to the T-antenna. Further, since the present invention includes an antenna distortion correction function and an in-band phase correction function, it is possible to increase the viability of hardware, and to reduce the manufacturing cost.

What is claimed is:

1. A millimeter wave image processor, comprising:
   antennas, arranged two-dimensionally, which receive a radio wave from a target;
   an A/D converter which A/D-converts a signal received by the antenna;
   a correlation processing unit which performs correlation processing to a combination of A/D-converted data signals; and
   an imaging processor which creates an image of the target by correlating an correlation processing output of signals received by the antennas with a reference function, the reference function being a received signal theoretically generated on an assumption that the target is at a position of a focused distance, for each pixel in a field of view.

2. The millimeter wave image processor, according to claim 1, further comprising, an in-band phase characteristic corrector which performs phase correction to an output of the A/D converter with a transversal filter by a phase correction function previously measured, and makes phase characteristics of vertical and horizontal antennas of a T-antenna coherent.

3. The millimeter wave image processor, according to claim 1, further comprising, an antenna phase characteristic corrector which compensates phase distortion of a received signal by using an antenna phase distortion correction function generated based on a difference between a phase of an observed value provided by reception processing from a calibration signal generator and a phase of a radio wave of a theoretical value.

4. The millimeter wave image processor, according to claim 1, wherein as the antennas, a T-antenna in which a plurality of antennas are arranged horizontally and vertically so as to be in T shape is used.

5. The millimeter wave image processor, according to claim 1, wherein as the antennas, antennas which are linearly moved horizontally and vertically so as to form a T-shaped trajectory to thereby receive a radio wave in a time divisional manner is used.

6. A millimeter wave image processing method, comprising the steps of:
   receiving a radio wave from a target;
   A/D converting a signal received;
   performing correlation processing to a combination of signals of a horizontal conversion output and a vertical conversion output among A/D converted data;
   on an assumption that the target is at a position of a focused distance, generating a theoretical received signal as a reference signal for each pixel in a field of view; and
   correlating an correlation output between antennas of spherical waves received by a T-antenna with the reference function, and performing matching and filtering steps to generate an image of the target.

7. The millimeter wave image processing method according to claim 6, comprising the step of forming a T-shaped trajectory by linearly moving multiple sets of antennas horizontally or vertically to thereby receive a radio wave.

* * * * *